United States Patent [19]
Manivannan et al.

[11] Patent Number: 6,099,127
[45] Date of Patent: Aug. 8, 2000

[54] SCANNING LASER OPHTHALMOSCOPE

[75] Inventors: Ayyakkannyu Manivannan, Aberdeen; Peter Frederick Sharp, Kincardinshire, both of United Kingdom

[73] Assignee: Aberdeen University, Aberdeen, United Kingdom

[21] Appl. No.: 09/254,388

[22] PCT Filed: Sep. 3, 1997

[86] PCT No.: PCT/GB97/02367

§ 371 Date: Jul. 27, 1999

§ 102(e) Date: Jul. 27, 1999

[87] PCT Pub. No.: WO98/09563

PCT Pub. Date: Mar. 12, 1998

[30] Foreign Application Priority Data

Jun. 9, 1996 [GB] United Kingdom .................... 9618691

[51] Int. Cl.⁷ .................................................. A61B 3/12
[52] U.S. Cl. ............................................. 351/221
[58] Field of Search ................................. 351/205, 206, 351/210, 211, 216, 220, 221, 209; 606/4; 372/38

[56] References Cited

U.S. PATENT DOCUMENTS

| | | | |
|---|---|---|---|
| 4,213,678 | 7/1980 | Pomerantzeff et al. .................... 351/7 |
| 4,781,453 | 11/1988 | Kobayashi .............................. 351/205 |
| 5,042,939 | 8/1991 | Zayek ...................................... 351/206 |
| 5,214,455 | 5/1993 | Penney et al. .......................... 351/210 |
| 5,396,302 | 3/1995 | Triller et al. ............................ 351/206 |
| 5,943,115 | 8/1999 | Ferguson ................................ 351/209 |
| 5,997,141 | 12/1999 | Heacock ................................. 351/221 |

FOREIGN PATENT DOCUMENTS

| | | |
|---|---|---|
| 0 428 450 A1 | 5/1991 | European Pat. Off. . |
| 0 428 450 B1 | 2/1995 | European Pat. Off. . |
| WO 98/09563 | 3/1998 | WIPO . |

OTHER PUBLICATIONS

Goldbaum, Michael H. et al., "The Discrimination of Similarly Colored Objects in Computer Images of the Ocular Fundus", *Investigative Ophthalmology & Visual Science*, vol. 31, No. 4, Apr. 1990, pp. 617–623.

*Primary Examiner*—George Manuel
*Attorney, Agent, or Firm*—Woodcock Washburn Kurtz Mackiewicz & Norris LLP

[57] ABSTRACT

An ophthalmoscope is disclosed comprising mirrors to generate a raster scan of laser light, and detect reflections of such light from the fundus of a patient's eye. The laser light originates from sources of at least three distinct wavelengths and is mixed to provide a single beam that, for each resolvable picture element of the raster scan, assumes in sequence each of the wavelengths. The reflected light is used to generate a multi-colored image of the fundus.

4 Claims, 3 Drawing Sheets

SCANNING LASER OPHTHALMOSCOPE

The present invention relates to an ophthalmoscope and more particularly to a scanning laser ophthalmoscope.

Various systemic diseases produce visible pathological features in the eye fundus. Thus, viewing of the eye fundus can provide an important indicator of these diseases.

A patient's fundus can be viewed by arranging for an image of the fundus to be directly projected onto an observer's retina. However, the small field of view, poor image quality and the need for correction of ametropia reduces the clinical value of the observation. In an alternative, a patient's fundus can be viewed by arranging for an illuminating beam to pass through the periphery of the pupil with the reflected light emerging through the centre of the pupil to provide an image of the fundus. However, it is necessary to dilate the pupil and use high levels of light which may be uncomfortable for patients.

To obtain a permanent record of the condition of the fundus and to assist in evaluation of the fundus, a so-called fundus camera is used to record the image of the fundus. The fundus camera can employ white light flash photography, but if monochromatic illumination is used instead, the contrast and optical quality is improved enabling better visualisation of certain fundus structures. Nevertheless, because objects of markedly different colours can be distinguished easily using colour information alone, colour photographs of the fundus are preferred with similarly coloured objects being differentiated on the basis of further details such as size, shape, etc.

Problems arise with the fundus camera for the reasons mentioned above. In particular, the high levels of light used reduces patient comfort. Thus, an ideal ophthalmoscope for observing the eye fundus would avoid the need to dilate the pupil and would minimise the intensity of light required to observe the eye fundus.

In the last 15 years, an ophthalmoscope for viewing the eye fundus known as a scanning laser ophthalmoscope (SLO) has been developed which comprises directing a narrow laser beam via a mirror system onto the eye fundus. The light reflected from the fundus is directed to a detector which produces an electrical output proportional to the intensity of the detected light. The electrical output can then be recorded or displayed on a visual display unit. By moving the mirror system according to a scanning sequence in a raster fashion and synchronising the detector to the scanning sequence, it is possible to produce an image of the fundus. Thus, it is not necessary to dilate the pupil. In addition, lower intensity illumination can be employed for viewing the eye fundus. However, care must be taken to ensure that the laser power is within the safety standards for retinal irradiation.

An object of the present invention is to provide an improved scanning laser ophthalmoscope.

According to the present invention there is provided an ophthalmoscope comprising:
 a laser beam means capable of providing respective laser beams having at least three different wavelengths;
 detector means capable of producing electrical signals according to light incident thereon;
 store means connected for receiving electrical signals from said detector means;
 an optical system for directing said laser beams to scan a selected portion of a patient's eye and for directing at least a portion of light reflected from said selected portion on to said detector means; and
 a control means capable of energising said laser beam means to periodically provide in sequence a single laser beam pulse of each wavelength and capable of operating said detector means to transfer said electrical signals to said store means at the completion of each laser beam pulse.

In this way, the detector means transfers to the store means the detection of the incident reflected light, from the selected portion of the patient's eye, which results from a single laser beam pulse, that is to say, the laser beam pulse of first one wavelength, then another wavelength and then another wavelength, in a sequence that is periodically repeated whilst the optical system directs the laser beams to scan that selected portion. As a result, an image of the selected portion is built up during a scan which comprises at least three different wavelength elements. By suitable manipulation of the stored electrical signals, the three wavelengths can be combined and if the correct wavelengths are selected, a colour image or colour representation of the selected portion can be produced. This colour image is produced without an increase in light intensity onto the selected portion compared with hitherto known scanning laser ophthalmoscopes because the laser beam pulse for each wavelength is only one third as long in the case of three wavelengths. Thus, safe levels of laser power are ensured whilst obtaining colour images. Furthermore, the advantages of colour that are obtained with photographs from a fundus camera can now be achieved with a scanning laser ophthalmoscope which avoids the problems of chromatic aberration and uncertainties of colour developing arising from a fundus camera. Finally, since the stored signals are in electrical form, direct computerised image analysis is possible.

It is preferred that the ophthalmoscope further comprises means for combining the electrical signals stored for each wavelength into a colour representation of said selected portion.

In this way, the ophthalmoscope can immediately provide a colour representation of the selected portion for long term storage or for reference, printing or display.

Conveniently, the ophthalmoscope further comprises a display means for displaying said colour representation.

By having a display means, the user of the ophthalmoscope can immediately check that it is operating properly and the patient can also see the colour representation of the selected portion.

To assess the severity of a disease and its response to treatment using photographs from a fundus camera or images from a hitherto known SLO, the patient's photographs or images are compared with a standard set of photographs or images. However, a large degree of skill and experience is required. In addition, the technique is labour intensive, susceptible to subjective observer variation and is relatively insensitive.

As an alternative, is has been proposed to use computer analysis. In this case with photographs, the standard photographs and the patient's photographs are projected onto a CCD camera and a frame grabber digitises the image for storage or analysis. By digitising the photographs, computer analysis can be employed. However, due to optical aberrations resulting from the fundus camera itself and the projection of the photographs onto the CCD camera, the digitised images require corrective techniques to be applied to them which reduces the reliability of the results from the computer analysis.

For these reasons, in one embodiment of the invention, the ophthalmoscope further comprises:
 archive means for storing colour representations of the selected portion of a healthy patient's eye which are produced by the ophthalmoscope; and analysis means for analysing a current colour representation with one or more colour representations stored in said archive means to identify differences therebetween.

Thus, by having an analysis means, the colour representation can have digital image processing techniques applied thereto enabling improved manipulation of what is effectively a colour image of the selected portion. By using colour representations from the ophthalmoscope of the present invention, the colour representations are already in electronic form for analysis. Thus, the problem of optical aberration errors associated with computer analysis of fungus camera photographs is not present. Moreover, by having colour representations of the selected portion, the advantageous differentiation of objects based on colour is maintained.

Examples of the present invention will now be described with reference to the accompanying drawings, in which.

Figure 1:
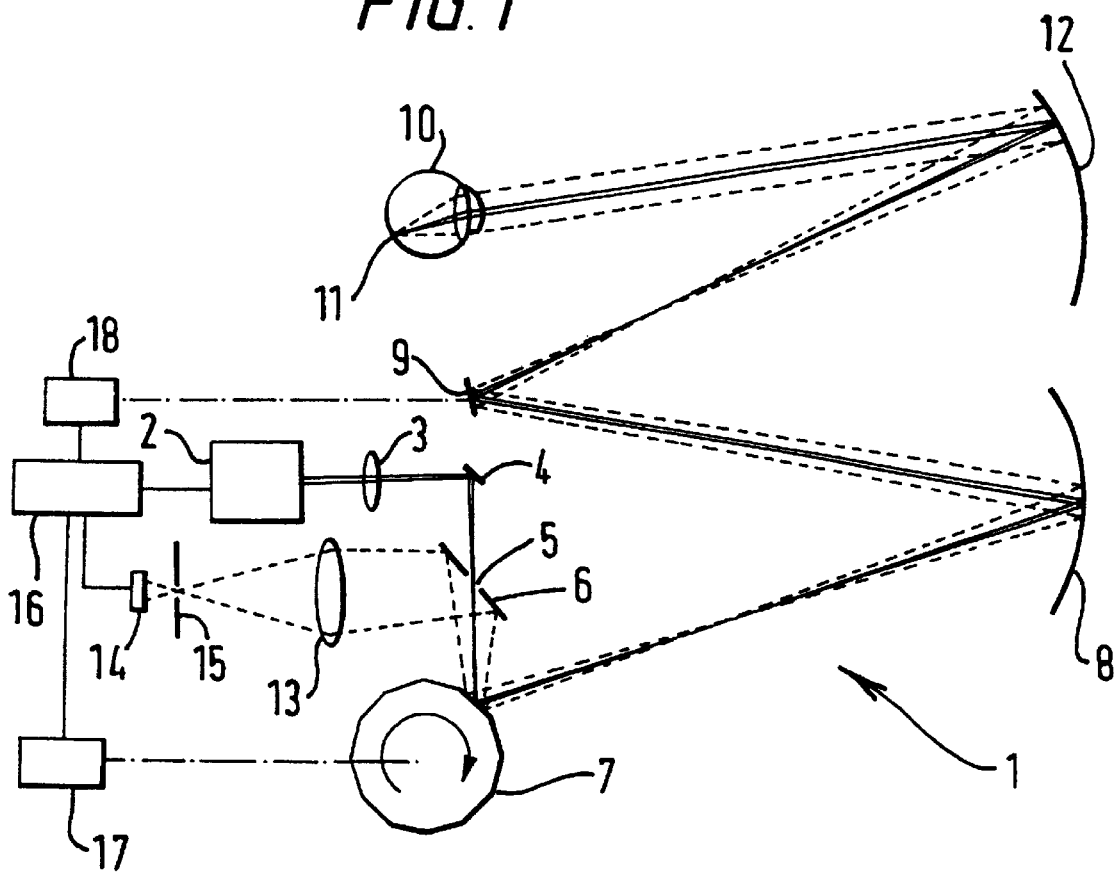
FIG. 1 illustrates an ophthalmoscope embodying the present invention.

FIG. 1 illustrates an ophthalmoscope 1 embodying the present invention. The ophthalmoscope has a laser beam means, in the form of a multiple laser source beam 2, comprising three separate laser beam sources, one capable of producing a beam of red laser light (670 nm wavelength), one capable of producing a beam of green laser light (540 nm wavelength) and one capable of producing a beam of blue laser light (488 nm wavelength) with the three sources being operated to produce only one beam at any particular time.

Figure 4:
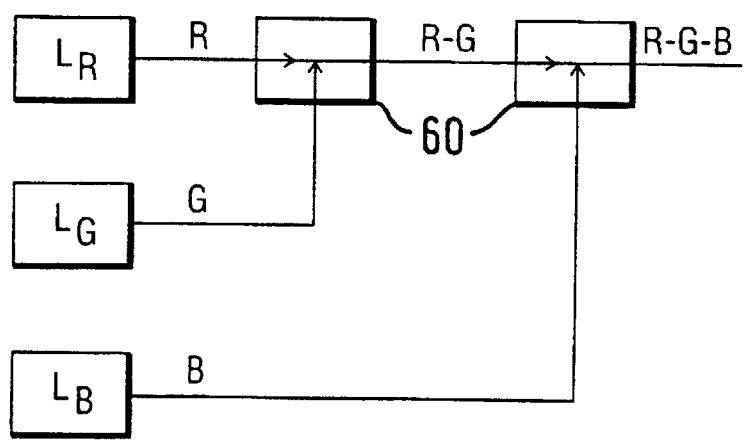
FIG. 4 illustrates an apparatus for combining three separate laser sources.

The scanning laser ophthalmoscope can accept only one laser beam in its optical axis. The three lasers LR, LG, LB are combined in the following way as shown in FIG. 4. The red laser beam R and the green laser beam G are first "added" using an optical beam adder 60. The resulting R-G beam is added to the blue laser beam B using another beam adder. The resulting R-G-B laser beam contains all the three wavelengths but at any single time (for a duration of one third of the total sampling period) only one laser beam is activated and the other two are disabled.

An optical system directs an emitted laser light beam pulse to a patient's eye 10 where it is incident at a point 11 on the fundus. The laser light beam enters the optical system through a lens 3, which is movable so that the laser light beam can be focused at the point 11, and is then reflected by a mirror 4 to pass through an aperture 5 in a mirror 6. The mirror 6 functions to split light from the laser beam source 2 from light reflected from the fundus.

The optical system further comprises a rotating polygon mirror 7 to reflect the laser light beam that is passing through aperture 5 on towards a mirror 8 as a line scan in a horizontal axis of the eye 10. The mirror 8 reflects and focuses the laser light beam at a point on a mirror 9. The mirror 9 is electrically movable so as to vary the reflection angle to product a scan in a vertical axis of the eye 10. The laser light beam is reflected by the mirror 9 to a mirror 12 which focuses the laser light beam onto the point 11. The focused laser light beam preferably has a diameter of 10 μm. Thus, the optical system directs the laser light beams to scan a selected portion of the patient's eye.

Light reflected from the point 11 emerges from the eye through a larger exit aperture than when incident and travels back along the same path and is de-scanned by the mirrors 9 and 7. The reflected light is then reflected by mirror 6 towards a lens 13 which focuses the reflected light onto a detector 14 located behind an aperture 15. The detector preferably takes the form of an avalanche photo-detector.

Thus, the optical system also directs at least a portion of the light reflected from the point 11 to be incident on the detector 14.

Figure 2:
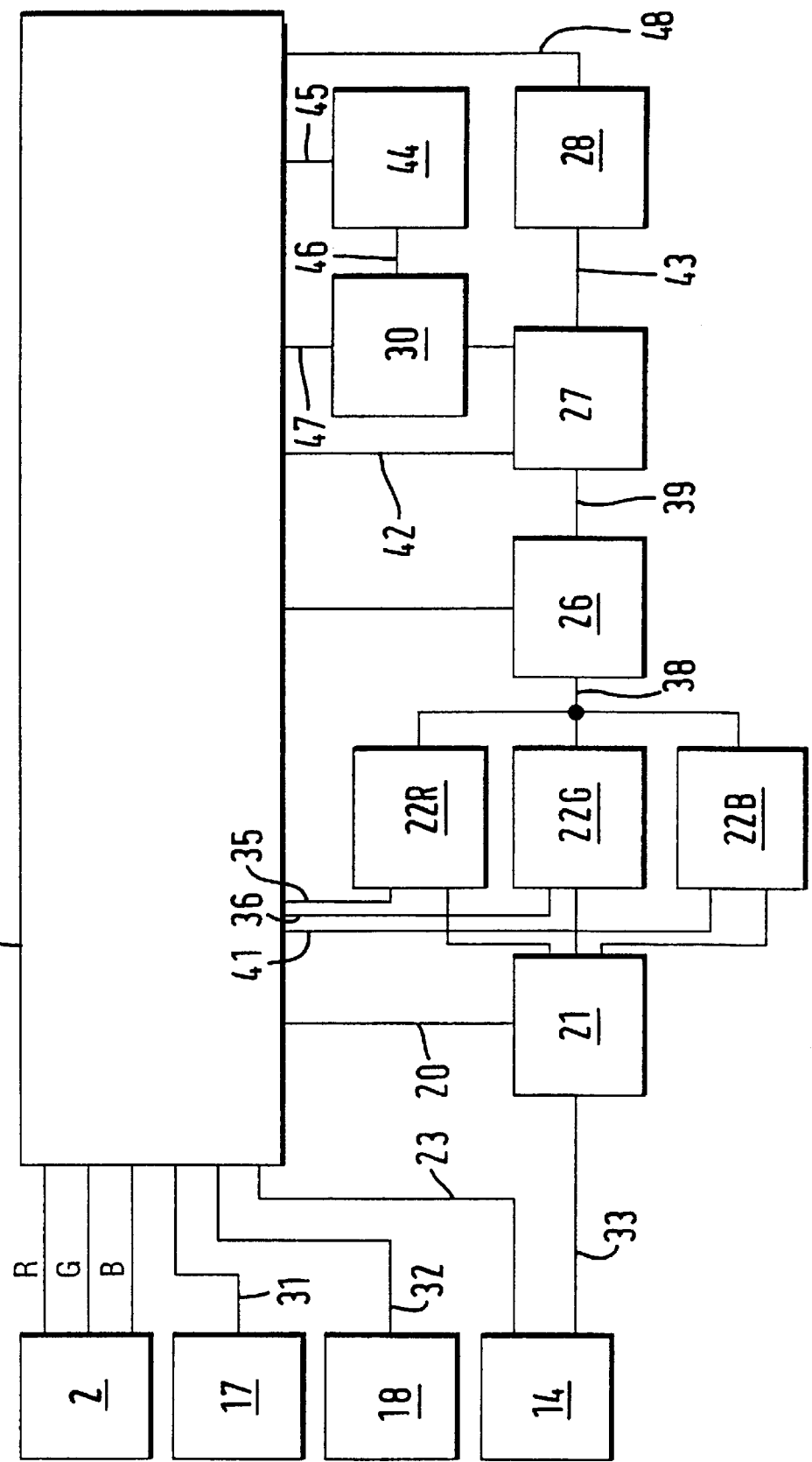
FIG. 2 illustrates in schematic form a control circuit of a first embodiment for operating the ophthalmoscope.

As shown in FIG. 2, in a first embodiment a control circuit 16 (identified in FIG. 1) comprises a microprocessor 37 which is connected by a line 31 to operate a motor 17 driving the polygon mirror 7 and by a line 32 to operate a motor 18 driving the mirror 9. The functional links between these motors and their respective mirrors are shown by a dot and dash line in FIG. 1. The microprocessor 37 is also connected to operate the laser beam source 2 and to operate the detector 14 as described below.

As is known in the art, an electronic colour image comprises a plurality of lines of pixels with groups of three pixels comprising red, blue and green. Referring to FIG. 2, the microprocessor 37 operates the laser beam source 2 to emit a pulse of red, green or blue laser light according to whether a signal appears on lines R, G or B. Effectively, the signal is present for a predetermined length of time so that the laser light is emitted for a predetermined length of time, that is say as a pulse.

At the time when a signal appears on line R, a signal briefly appears on a line 20 connected to a rotary switch 21. As a result, electrical signals at an input of the switch 21 are routed to a red store 22R. A subsequent signal briefly appearing on line 20 will change the connection of the rotary switch 21 so that electrical signals at the input thereof are routed to a green store 22G. A subsequent signal briefly appearing on line 20 will change the connection of the rotary switch 21 so that electrical signals at the input thereof are routed to a blue store 22B.

When the microprocessor 37 makes a signal appear on line R, the microprocessor 37 counts the passing of a predetermined time interval corresponding to the red laser light beam pulse length. At the same time, the microprocessor ensures that the switch 21 connects electrical signals at the input of the switch to the red store 22R. When the predetermined time interval has passed, a transfer signal is sent along a line 23 connected to the detector 14 so that the contents thereof, which are proportional to the intensity of light received during the predetermined time interval of emission of the red laser light, are transferred to the input of the switch 21 via a line 33 and the detector is reset. Accordingly, the detector contents received during the emission of the red laser light are stored as a single pixel at a predetermined location of the red store 22R.

The microprocessor 37 then makes a signal appear on line G and starts counting the passing of a predetermined time interval again which corresponds to the green laser light beam pulse length. At the same time, a signal briefly appears on line 20 to ensure that the switch 21 is changed so that electrical signals at the input of the switch are routed to the green store 22G. When the predetermined time interval has passed, a transfer signal is sent along the line 23 so that the contents of the detector, which are proportional to the intensity of light received during the predetermined time interval of emission of the green laser light, are transferred along the line 33 to the input of the switch 21 and the detector is reset. Accordingly, the detector contents received during the emission of the green laser light are stored as a single pixel at a predetermined location of the green store 22G.

The microprocessor 37 then makes a signal appear on line B and starts counting the passing of a predetermined time interval again which corresponds to the green laser light beam pulse length. At the same time, a signal briefly appears on line 20 to ensure that the switch 21 is changed so that electrical signals at the input of the switch are routed to the blue store 22B. When the predetermined time interval has passed, a transfer signal is sent along the line 23 so that the contents of the detector, which are proportional to the intensity of light received during the predetermined time interval of emission of the blue laser light, are transferred to the input of the switch 21 and the detector is reset. Accordingly, the detector contents received during the emission of the blue laser light are stored as a single pixel at a predetermined location of the blue store 22B.

This sequence of emission of red, green and blue laser light is repeated whilst a saw tooth signal, typically of 50 Hz, is applied to the motor 18 to cause a vertical scan by the mirror 9 and whilst power is applied to motor 17 to rotate the mirror 7 to cause a line scan typically at 15625 Hz.

Thus, stores 22R, 22G and 22B, are synchronised to gradually store a complete image of red, green and blue light reflected from point 11 as it scans across the fundus. During storage of the electrical signals in stores 22R, 22G and 22B, the microprocessor 37 activates these stores in sequence via lines 35, 36 and 41 to transfer the stored electrical values to a frame store 26 via a line 38 so that a complete colour representation or colour image of the fundus is built up therein. Consequently, the image in the stores 22R, 22G and 22B are continuously overwritten.

A frame grabber 27 connected to the frame store 26 via a line 39 then takes the complete colour representation and drives a display 28 via a line 43 to display the colour representation of the fundus. If a signal appears on a line 42, then a main store 30 digitises and stores the current complete current colour representation contained in the frame grabber 27.

The microprocessor 37 is also connected to an archive 44 via a bus 45 and is connected to the main store 30 via a bus 47. The archive is also connected to the main store 30 via a bus 46. Thus, representations stored in the main store 30 can also be transferred for storage in archive 44.

Accordingly, when a colour representation of the fundus of a healthy patient is obtained, that "healthy" representation can be stored in archive 44 as a healthy colour representation.

The microprocessor 37 can be programmed with image analysis software. Thus, a current representation stored in main store 30 can be compared with a "healthy" representation stored in archive 44 and the comparison results displayed on display 28 via line 48. Since different coloured objects can be easily distinguished and since optical aberration effects do not arise because the colour representations of the fundus are produced in electrical form directly from the light reflected from the fundus, a more reliable indicator of disease can be obtained with the ophthalmoscope of the present invention.

Figure 3:
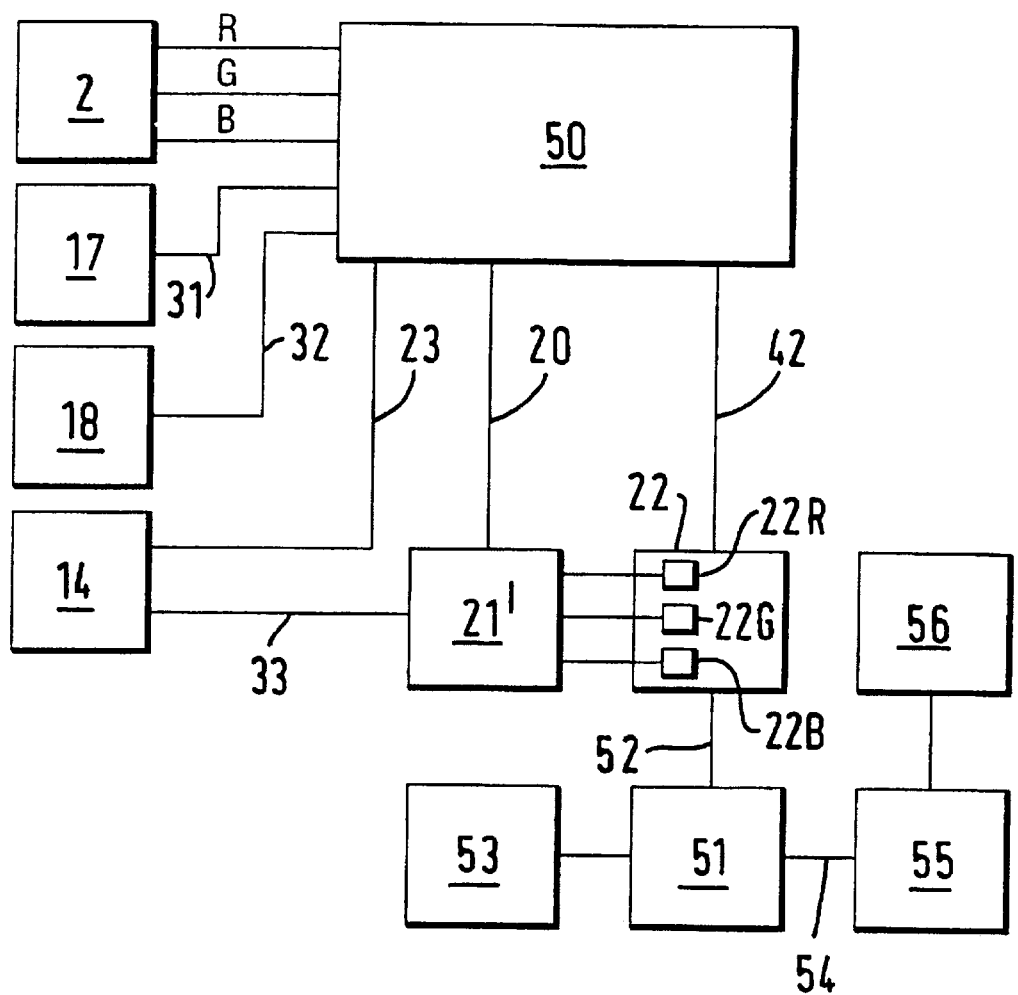
FIG. 3 illustrates in schematic from a control circuit of a second embodiment for operating the ophthalmoscope.

As shown in FIG. 3, in a second embodiment the microprocessor of the first embodiment is replaced with a clock signal generator 50. At the time when a signal appears on line R, a signal briefly appears on a line 20 connected to electronic switch 21'. As a result, electrical signals at an input of the switch 21' are routed to a red store 22R, which is the red memory buffer and part of a frame grabber 22. A subsequent signal briefly appearing on line 20 will change the connection of other electronic switch 21' so that electrical signals at the input thereof are routed to a green store 22G, which is the green memory buffer of the frame grabber 22. A subsequent signal briefly appearing on line 20 will change the connection of the electronic switch 21' so that electrical signals at the input thereof are routed to a blue store 22B, which is the blue memory buffer of the frame grabber 22.

Stores 22R, 22G and 22B, are synchronised to gradually store a complete image of red, green and blue light reflected from point 11 as it scans across the fundus. The frame grabber 22 then can combine the red, green and blue buffer images into a single colour image. The frame grabber is connected to a computer, for example an IBM compatible Personal Computer 51, through a PCI bus 52, and can transfer the colour image to the hard disk. The personal computer is connected through network 54, to for example, a UNIX based SUN Sparc station 55, with an optical storage device 56. The optical device is used as the image main store.

The SUN Sparc station can be equipped with a powerful image analysis software (visilog) which allows comparison of images of patients obtained at various visits.

It will be understood that the embodiments illustrated show applications of the invention in certain forms only for the purposes of illustration. In practice, the invention may be applied to many different configurations, the detailed embodiments being straightforward for those skilled in the art to implement. For example, as an alternative or in addition to display 28, a printer (not shown) can be provided as an output device.

What is claimed is:

1. An ophthalmoscope comprising:
   a laser beam means capable of providing respective laser beams having at least three different wavelengths;
   detector means capable of producing electrical signals according to light incident thereon;
   store means connected for receiving electrical signals from said detector means;
   an optical system for directing said laser beams to scan a selected portion of a patient's eye in a point-by-point sequence and for directing at least a portion of light reflected from said selected portion on to said detector means; and
   a control means capable of energising said laser beam means to provide in sequence, and for each said point in turn, a single laser beam pulse of each wavelength and capable of operating said detector means to transfer said electrical signals to said store means at the completion of each laser beam pulse.

2. An ophthalmoscope according to claim 1 further comprising means for combining the electrical signals stored for each wavelength into a colour representation of each said point of said selected portion.

3. An ophthalmoscope according to claim 2 further comprising a display means for displaying said colour representation.

4. An ophthalmoscope according to claim 2 further comprising:
   archive means for storing colour representations of the selected portion of a healthy patient's which are produced by the ophthalmoscope; and
   analysis means for analysing a current colour representation with one or more colour representations stored in said archive means to identify differences therebetween.

* * * * *

UNITED STATES PATENT AND TRADEMARK OFFICE
CERTIFICATE OF CORRECTION

PATENT NO. : 6,099,127
DATED : 08/8/00
INVENTOR(S) : Manivannan et al.

It is certified that error appears in the above-identified patent and that said Letters Patent is hereby corrected as shown below:

Col. 3, line 11, change "fungus" to --fundus--; (PTO)

Col. 3, line 22, change "from" to --form--. (OUR)

Signed and Sealed this

Seventeenth Day of April, 2001

Attest:

NICHOLAS P. GODICI

Attesting Officer    Acting Director of the United States Patent and Trademark Office